United States Patent
Moré

(10) Patent No.: US 10,369,135 B2
(45) Date of Patent: Aug. 6, 2019

(54) FORMULATIONS FOR TREATMENT OF HYPERTHYROIDISM

(71) Applicant: DENDROPHARM GMBH, Berlin (DE)

(72) Inventor: Sam Moré, Dresden (DE)

(73) Assignee: DENDROPHARM GMBH, Berlin (DE)

( * ) Notice: Subject to any disclaimer, the term of this patent is extended or adjusted under 35 U.S.C. 154(b) by 99 days.

(21) Appl. No.: 15/311,030

(22) PCT Filed: May 12, 2015

(86) PCT No.: PCT/DE2015/100192
§ 371 (c)(1),
(2) Date: Jan. 12, 2017

(87) PCT Pub. No.: WO2015/172769
PCT Pub. Date: Nov. 19, 2015

(65) Prior Publication Data
US 2017/0143675 A1  May 25, 2017

(30) Foreign Application Priority Data
May 13, 2014  (DE) ........................ 10 2014 106 749

(51) Int. Cl.
| | |
|---|---|
| *A01N 43/50* | (2006.01) |
| *A61K 31/415* | (2006.01) |
| *A61K 31/4164* | (2006.01) |
| *A61K 9/00* | (2006.01) |
| *A61K 47/14* | (2017.01) |
| *A61K 47/32* | (2006.01) |
| *A61K 47/44* | (2017.01) |
| *A61K 31/164* | (2006.01) |
| *A61K 31/355* | (2006.01) |

(52) U.S. Cl.
CPC ........ *A61K 31/4164* (2013.01); *A61K 9/0014* (2013.01); *A61K 9/0017* (2013.01); *A61K 9/0046* (2013.01); *A61K 31/164* (2013.01); *A61K 31/355* (2013.01); *A61K 47/14* (2013.01); *A61K 47/32* (2013.01); *A61K 47/44* (2013.01)

(58) Field of Classification Search
USPC .......................................................... 514/392
See application file for complete search history.

(56) References Cited

U.S. PATENT DOCUMENTS

| | | | | |
|---|---|---|---|---|
| 6,365,616 B1* | 4/2002 | Kohn | ................. | A61K 31/4164 514/396 |
| 8,124,128 B2* | 2/2012 | Hsieh | ................... | A61K 9/1075 424/46 |
| 2003/0161849 A1* | 8/2003 | Heidenfelder | ........... | A61K 8/06 424/401 |
| 2010/0137389 A1 | 6/2010 | Nanjan et al. | | |
| 2013/0203847 A1* | 8/2013 | Chappell | ............. | A61K 9/0014 514/533 |

FOREIGN PATENT DOCUMENTS

| | | |
|---|---|---|
| CN | 1085079 A | 4/1994 |
| CN | 1692940 | * 11/2005 |
| EP | 2923695 | 9/2015 |
| WO | 2006018295 | 2/2006 |
| WO | 2008009562 | 1/2008 |

OTHER PUBLICATIONS

Fleige et. al. (Nanocarriers (2013) 1:1-19).*
Buijtels et al., Carbimazolzalf ter behandeling van hyperthyreoidie bij de kat, Tijdschrift voor Diergeneeskunde 131 (31):478-482, 2006.
Fleige et al., Aggregation Phenomena of Host and Guest upon the Loading of Dendritic Core-Multishell Nanoparticles with Solvatochromic Dyes, Macromolecules 45, 9452-9459, 2012.
Fleige et al., Dendronized core-multishell nanocarriers for solubilization of guest molecules, Nanocarriers, vol. 1, 1-9, 2013.
Haag et al., An Approach to Core-Shell-Type Architectures in Hyperbranched Polyglycerols by Selective Chemical Differentiation, Macromolecules 33, 8158-816, 2000.
Haag et al., Skin penetration enhancement of core—multishell nanotransporters and invasomes measured by electron paramagnetic resonance spectroscopy, International Journal of Pharmaceutics 416, 223-228, 2011.
Hoffmann et al., Transdermal methimazole treatment in cats with hyperthyroidism, Journal of Feline Medicine and Surgery 5,77-82, 2003.
Hoffmann et al., Bioavailability of transdermal methimazole in a pluronic lecithin organogel(PLO)in healthy cats, J. Vet. Pharmacol. Therap. 25, 189-193, 2002.
Lécuyer et al., Clinical efficacy and safety of transdermal methimazole in the treatment of feline hyperthyroidism, Can Vet J 47, 131-135.
Radowski et al., Supramolecular Aggregates of Dendritic Multishell Architectures as Universal Nanocarriers**, Angew. Chem. Int. Ed. 46, 1265-1269, 2007.

(Continued)

*Primary Examiner* — Marcos L Sznaidman
(74) *Attorney, Agent, or Firm* — Thomas|Horstemeyer, LLP

(57) ABSTRACT

The present invention relates to compositions, in particular for the treatment of hyperthyreosis (also designated hyperthyroidism), especially in cats. These compositions are formulated for transdermal administration of an active substance and may, for example, be applied into the auricle (or pinna) of the cat. They comprise an active agent such as methimazole (or 2-mercapto-1-methylimidazole) or carbimazole, at least one wax, at least one fatty oil, and optionally an emulsifier. As emulsifier a nanocarrier may be used, for example. Unimolecular nanocarriers of dendritic structure are preferred, wherein the nanocarrier comprises a dendritic core and at least two shells, wherein an inner shell is coupled to the dendritic core via a first linker, and an outer shell is coupled to the inner shell via a second linker. In one embodiment, the composition is provided as a stick, in another, a semi-solid formulation in a suitable applicator which may contain one or more dosage units.

15 Claims, No Drawings

(56) References Cited

OTHER PUBLICATIONS

Sartor et al., Efficacy and Safety of Transdermal Methimazole in the Treatment of Cats with Hyperthyroidism, J Vet Intern Med 18, 651-655, 2004.
Trepanier, Pharmacologic Management of Feline Hyperthyroidism, Vet Clin Small Anim 37, 775-788, 2007.
Chinese Office Action for Application 201580038243.7, dated Jan. 2, 2019.

* cited by examiner

FORMULATIONS FOR TREATMENT OF HYPERTHYROIDISM

The present invention relates to compositions, in particular for the treatment of hyperthyreosis (also designated hyperthyroidism), especially in cats. These compositions are formulated for transdermal administration of an active substance and may, for example, be applied into the auricle (or pinna) of the cat. They comprise an active agent such as methimazole (or 2-mercapto-1-methylimidazole) or carbimazole, at least one wax, at least one fatty oil, and optionally an emulsifier. As emulsifier a nanocarrier may be used, for example. Unimolecular nanocarriers of dendritic structure are preferred, wherein the nanocarrier comprises a dendritic core and at least two shells, wherein an inner shell is coupled to the dendritic core via a first linker, and an outer shell is coupled to the inner shell via a second linker. In one embodiment, the composition is provided as a stick. In a further embodiment, the composition is provided as a semi-solid formulation in a suitable applicator which may comprise one or more dosage units.

Hyperthyreosis is a pathological hyperactivity of the thyroid, which manifests in excessive production of thyroid hormones, so that a corresponding oversupply is produced within the organism. Consequently, a variety of symptoms such as severe sweating, rapid heartbeat, weight loss, nervousness and tremor can occur. The most common causes of hyperthyreosis in humans are Graves' disease and thyroid autonomy, both associated with an increased secretive function of the thyroid gland, as well as an increased intake of thyroid hormones in the form of drugs (Thyreotoxicosis factitia). An extreme form of life threatening overfunction is called "thyrotoxic crisis" (synonymous with thyrotoxicosis, "thyroid hormone poisoning") (wikipedia).

Hyperthyroidism does not only occur in people, but also in animals. It is the most common endocrine disorder of the cat. Treatment options are radioiodine therapy, thyroidectomy or drug treatment. During drug therapy those affected are prescribed antithyroid drugs, which inhibit the formation of thyroid hormones, for as long, and in an amount so that a normalization of laboratory values (euthyreosis) is achieved. Frequently, sulphurous antithyroid drugs (propylthiouracil, carbimazole, methimazole and others) are used, which however have a latency period of approximately oneweek. If a fast onset of action is necessary, sodium perchlorate, which inhibits the uptake of iodine into the thyroid gland, may be used. Antithyroid drugs are ineffective if hyperthyreosis is caused by an inflammation of the thyroid gland (thyroiditis), since they cannot influence the release of the hormones stored in the thyroid ("preformed hormones") due to the inflammatory process, but they work well for other causes of hyperthyreosis. Propranolol (a non-cardioselective β-blocker) can be used additionally in tachycardia, but also alleviates the non-cardiac symptoms of hyperthyreosis and inhibits the conversion from $T_4$ to $T_3$.

Radiotherapy is costly and irreversible. Kidney problems, which often also exist in older cats, are exacerbated by the failure of the thyroid gland, thus, a well-controlled drug treatment that allows a variable dosing with methimazole/carbimazole, is more advantageous, because the blood pressure can remain slightly increased: the kidney is flushed better. In many countries, drug treatment is the treatment of choice. Carbimazole, a thiourea derivative, is a prodrug and is converted into its active form methimazole immediately after resorption.

Methimazole and carbimazole are usually also used before radiation therapy or thyroidectomy (especially in humans). Both agents can be used in cats with renal insufficiency for long-term therapy, or as a test to find out whether serum T4 can be safely lowered by irradiation or by a thyroidectomy without leading to a renal insufficiency with renal failure, which is difficult to treat. Methimazole inhibits thyroid peroxidase, an enzyme which plays a role in the oxidation of iodide to elemental iodine, the incorporation of iodine into thyreoglobulin and the incorporation of tyrosyl residues as well as their combination to form $T_3$ and $T_4$.

Typically methimazole is administered orally, wherein in humans a once daily dose is usually sufficient. In cats, it has been shown that administration twice a day is more effective than once a day (Trepanier, 2007 Vet Clin Small Anim 37: 775-788). Treatment with carbimazole must also be performed daily. In approximately 20% of treated cats, the oral administration leads to side effects (especially vomiting, lethargy, pruritus, liver disease, changes in blood count), which mostly disappear after discontinuation of the drug. Vomiting, anorexia and lethargy occurs in approximately 10%-18% of cases of oral administration of methimazole. Transdermal administration of methimazole is associated with significantly fewer gastrointestinal side effects than oral administration (Sartor et al, 2004 J Vet Intern Med. 18: 651-655). The drug is usually applied by the owner of the cat to the inner side of the pinna, whereby a contact with the skin of the holder should be avoided, normally by wearing gloves or finger cots. So far there is no approved transdermal carbimazole or methimazole formulation in the EU.

So far, methimazole is predominantly administered transdermally in pluronic lecithin organogel (PLO). PLO acts as a permeation enhancer through the stratum corneum. Although it was shown that the transdermal uptake of methimazole after a single dose in PLO was poor (Hoffmann et al, 2002, J. Pharmacol Therap. 25:189-193), chronic transdermal administration was effective for reduction of the serum $T_4$ concentration (Lecuyer et al, 2006 Can J Vet 47:131-135, Hoffmann et al, 2003, Journal of Feline Medicine and Surgery 5: 77-82). In a randomized trial, only 4% instead of 24% (oral administration) of cats had gastrointestinal side effects (Sartor et al, 2004 J Vet Intern Med. 18: 651-655).

Disadvantages of administering methimazole in PLO are poor absorption, redness at the application site, increased formulation cost and unclear stability of the composition. (Sartor et al, 2004 J Vet Intern Med. 18: 651-655, Trepanier, 2007 Vet Clin Small Anim 37: 775-788).

A formulation of methimazole is described in the withdrawal assessment report for Nexcyon Pharmaceuticals Ltd and Enthryv (EMEAN/C/002808/0000). An ethanolic solution of methimazole containing octisalate and padimate-O as a penetration enhancer or penetration modulator was used. The dosage options were 0.25 ml (18.75 mg), 0.5 ml (37.5 mg) or 0.75 ml (56.25 mg methimazole), which was to be administered transdermally every 2 to 3 days. The amounts applied were 0.25 ml, 0.5 ml and 0.75 ml, respectively. However, the efficacy of the treatment was assessed as not equivalent to oral therapy. Furthermore, there was no user safety, because the methimazole residues in the coat of the cat were too high.

Buijtels et al, 2006 (Tijdschrift voor Diergeneeskunde 131 (13): 478-482) describe a formulation for the transdermal administration of carbimazole in an eye ointment with lecithin. However, the use of lecithin is not desirable, since this makes the formulation tacky and difficult to apply, and it further does not have good absorption characteristics.

US 2010/0137389 A1 describes an anti-hyperthyroid composition for transdermal administration, comprising at least one aprotic polar solvent, at least one polyol, in particular PEG4000, and at least one fatty acid. Disadvantages of the examples for formulation described in the application are, for example, the high content of oxidation-sensitive oleic acid, and the high content of propylene glycol, which can lead to skin irritation in the amounts described (>35%). Furthermore, NMP is proposed as penetration enhancer, here there is also a risk of skin irritation.

Buijtels et al, 2006, and US 2010/0137389 A1 teach that it is often difficult to find a formulation for an active agent with a penetration enhancer, penetration modulator or tractor which has suitable properties, as this needs to be tested individually for each active agent, and for each desired drug-release-profile. The characteristics as penetration enhancer are thus specific for each active agent or each drug-release-profile, or at least only predictable for closely related active substances with similar physico-chemical characteristics.

In contrast, the inventors put themselves to the task of providing a new composition for the transdermal delivery of methimazole and/or carbimazole, which preferably overcomes at least some of these disadvantages. Furthermore, it is advantageous from the point of view of the user to apply an amount as small as possible both of active agent and the ointment formulation containing the active agent. This is due to the fact that the active substance is teratogenic, and therefore must not be taken up by the cat holder. The risk associated with this is lowered by the small amounts applied, i.e., 25-100 µl as a typical application quantity for cats with an average decrease of TT4 value. These applied amounts are up to 75% lower than the amount described in the literature for previous dermal formulations. This task is solved by the present invention, especially by the object of claims.

The object of invention is a composition comprising
a) an active substance selected from the group consisting of methimazole and/or carbimazole;
b) at least one wax selected from the group comprising beeswax, lanolin, carnauba wax, paraffin wax, Candelilla wax, cetyl palmitate, berry wax, Chinese wax, Japan wax, jojoba oil or polyethylene glycol; and
c) at least one fatty oil selected from the group comprising peanut oil, almond oil, sunflower oil, linseed oil, olive oil, evening primrose oil, castor oil or mineral oil.

The active substance methimazole is preferred. Carbimazole also can be used, which acts as a prodrug of methimazole.

Waxes are materials that are defined by their mechanical-physical properties. Their chemical composition and origin, however, is very different. A substance is called wax when it can be kneaded at 20° C., is solid to brittle hard, has an amorphous to fine-crystalline structure which is colour-translucent to opaque, but not glassy; when it melts above 40° C. without decomposition, is slightly liquid (with low viscosity) slightly above the melting point, has a highly temperature-dependent consistency and solubility and can be polished under light pressure. Animal and vegetable waxes are waxes in the narrower sense, they are counted among the lipids. Main components of these mixtures are generally esters of fatty acids (also called wax acids) with long-chain, aliphatic, primary alcohols, the so-called fatty alcohols. These esters differ in structure from the fats and fatty oils, which are triglycerides with fatty acids. In addition, these waxes contain free, long-chain aliphatic carboxylic acids, ketones, alcohols and hydrocarbons (Wikipedia).

The wax used in the invention may be a vegetable, animal or synthetic wax, for example, beeswax, in particular Cera alba or Cera flava, wool wax, lanolin (a wool wax-containing composition), carnauba wax, paraffin wax, Candelilla wax, cetyl palmitate, berry wax, Chinese wax, Japan wax, jojoba oil, polyethylene glycol or a combination thereof. In the context of the invention, polyethylene glycol (PEG) is also referred to as wax, in particular with a molecular weight of more than 400 Da, preferably more than 500 or more than 600 Da, up to approximately 35 000 Da. PEG with a molecular weight between 200 and 400 Da are non-volatile liquids at room temperature (approximately 20° C.). PEG 600 has a melting range of 17 to 22° C., and thus a paste-like consistency. At molecular weights more than 3 000, PEGs are solid substances and are commercialised as flakes or powder. Hardness and melting range increase with increasing molecular weight. Mixing a solid PEG (eg PEG 1500) with a liquid PEG allows the production of a water-soluble product of an ointment-like consistency. By mixing, the consistency of the composition can be adjusted as desired. Preferably, at least one of the waxes used is solid or viscous at room temperature (20° C.).

The fatty oil preferably is peanut oil, almond oil, sunflower oil, linseed oil, olive oil, evening primrose oil, castor oil or mineral oil. Mineral oil is a hypoallergenic oil advantageous for especially sensitive skin. Almond oil is also preferred.

Optionally, the composition of the invention includes an additional emulsifier. Surprisingly, it has been found that the active substance itself acts as an emulsifier, and the addition of an additional emulsifier is not therefore necessary.

However, a further emulsifier may also be added. Such additional emulsifier may be polyvinylpyrrolidone (PVP), cetylstearyl alcohol, propylene glycol, an amphiphilic nanocarrier or a combination thereof. PEG can also act as an additional emulsifier. Cetylstearyl alcohol is a mixture of cetyl alcohol (hexadecanol) and stearyl alcohol (octadecanol), which increases the stability of emulsions and can improve the texture of preparations.

The emulsifier preferably also acts as a penetration enhancer or tractor. In a preferred embodiment, the emulsifier is polyvinylpyrrolidone, preferably having a molecular weight from 2,500 to 100,000 Da, 5000 to 40,000 Da, in particular from approximately 8000 to 20,000 Da, or from 10,000 to 15,000 Da. Preferably, propylene glycol is avoided or substantially avoided, as this can lead to skin irritation, especially in larger concentrations.

In one embodiment, an amphiphilic nanocarrier is used as an emulsifier or as penetration modulator, in particular a unimolecular nanocarrier of dendritic structure, wherein the nanocarrier is preferably composed of a dendritic core and at least two shells, wherein an inner shell is coupled to the dendritic core via a first linker, and an outer shell is coupled to the inner shell via a second linker. In one embodiment, the nanocarriers are neutral or anionic. Corresponding nanocarriers are e.g. disclosed in WO 2006/018295 A2. Nanocarriers disclosed in Radowski et al (Angew Chem Int Ed 2007 46, 1265-1269); Fleige et al. (Macromolecules 2012, 45, 9452-9459), Fleige et al. (Nanocarriers, Vol. 1, 2013, 1-9, WO2011/095311), or Haag et al. (Macromolecules, 2000, 33, 8158-8166) can also be used in the context of the invention. A unimolecular sulfated polyanionic nanocarrier, especially a unimolecular polyanionic polyglycerol micelle with a hydophilic shell and a hydrophobic core (EP application no. 14 161 579.9) can also be used.

The nanocarrier may be configured such that
a) the dendritic core of the nanocarrier is made of polyglycerol, preferably with a molecular weight of 3-20 kDa, more preferably 7-10 or 8-9 kDa; and/or b) the inner shell of the nanocarrier is a preferably linear alkyl chain with a carbon length of C2 to C40, preferably C8-014 or 010-C12; and/or c) the outer shell is polyethylene glycol having the structural formula (—CH$_2$—CH$_2$O—)$_n$, with n=3–130, which bears a terminal methyl group, a hydroxyl group or a carboxyl group, preferably a methyl group and/or d) the first linker is an ester or amide linkage; and/or e) the second linker is an ester bond, wherein preferably all features of a-e apply.

The nanocarriers may comprise dendritic polyglyceroldo-decanic acid polyethylene glycolate. It can be characterized by way of example as follows:

Nomenclature formula: hPG$_{10000}$(—NH$_2$)$_{0.7}$(C$_{12}$ mPEG$_{350}$)$_{1.0}$ (Mn=350)

Alternative nomenclature: hPG$_{10000}$(—NH$_2$)$_{0.7}$(C$_{12}$ mPEG$_6$)$_{1.0}$ (6 repeating units on average)

hPG10k has approximately 135 functional groups, approximately 40-80% of them, for example approximately 70% having reacted to amines (index number 0.7).

| Molecular constituents from the inside to the outside: | Chemical component size | Synthesis module |
|---|---|---|
| 1. Dendritic core | hyperbranched polyglycerol = hPG M$_n$ = 8000-10000 Da | hyperbranched polyglycerolamin = hPG(—NH$_2$) (M$_n$ = 10 kDa, 40-80% amination, particularly 65-70%) |
| | peptide bond | |
| 2. Lipophilic nonpolar layer of saturated fatty acids | C$_{10}$ or C$_{12}$-fatty acid chain, in particular C$_{12}$ | C$_{10}$-diacid: 1,10-decanic acid or C$_{12}$-diacid: 1,12-dodecanic acid |
| | ester bond | |
| 3. Hydrophilic polyethylene glycol chain | mPEG = methoxypolyethylene glycol; M$_n$ = 350 | mPEG = methoxypolyethylene glycol; M$_n$ = 350, 500, 700 or 1000, in particular 350 |

The nanocarriers can aggregate and can absorb guest molecules (e.g., the active agent) during this aggregation. Unimers and aggregates are in an equilibrium, which shifts with increasing dilution in direction of unimers, but with slow kinetics. In addition, especially depending on polarity and pH of the environment, a release of the guest molecules from the aggregates takes place. Therefore, the nanocarrier does not only act as emulsifier but also as a permeation modulator, improving, on the one hand, the kinetics of drug release, and, on the other hand, helping to overcome the dermal barrier. Due to an interaction with the stratum corneum, an optimal insertion into upper layers of skin with subsequent favorable release profile can be achieved.

Preferably, a composition of the invention comprises 2.5-15% w/w methimazole, preferably approximately 10-15% w/w or 11-12% w/w methimazole, or approximately 5 to 20% w/w carbimazole. The preferred concentration of carbimazole can be approximately 1.6-2 times as high as the preferred methimazole concentration, or alternatively approximately 1.6-2 times of the amount will be administered.

In a preferred embodiment, an inventive composition comprises a) 2.5-15% w/w methimazole and/or 5-20% w/w carbimazole, preferably methimazole;

b) 5-18% w/w wax, preferably approximately 12-16% w/w, or approximately 14.3% w/w;

c) 45-70% w/w fatty oil, preferably approximately 60-70%, or approximately 67.5% w/w;

d) 0-25% w/w emulsifier.

If the emulsifier is a nanocarrier, the composition of the invention may, for example, comprise 0.05-25% (w/w) of the nanocarrier, preferably approximately 1-5% (w/w), approximately 0.25 to 3.5% (w/w) or approximately 0.5% (w/w). For other emulsifiers, for example PVP, the concentration is preferably higher, for example, 1-10%, preferably approximately 5-8% w/w, or approximately 6.5-7% w/w. Of course, the nanocarrier and other emulsifiers, for example, PVP, may be combined, e.g. in the amounts mentioned.

The composition may include further excipients, active substances, for example dexpanthenol, or carriers, for example, water or ethanol, however, this is not necessary. The composition can thus be free of water. Preferably, the composition is free of water, PEG and propylene glycol.

Addition of a tocopherol derivative (vitamin E or antioxidatively active derivatives thereof), e.g., in a concentration of 0.01-0.5%, preferably 0.02-0.2% w/w, or another skin-friendly antioxidant is preferred.

In one embodiment, the composition of the invention is a grease stick or comprises it. When using a grease stick for administration, the contact with the skin of the user (e.g. the cat holder or nursing staff) is minimized, so that, preferably, protective measures such as gloves or finger cots are no longer needed. This simplifies the application and increases, particularly for the treatment of animals such as cats, compliance. It has been found that animals such as cats tolerate the application of a grease stick very well.

The grease stick can be fixed within a holding and dosing device, which may be similar to a lipstick case. In this case, e.g., by applying a defined rotation, this grease stick can be advanced by a defined length, which corresponds to a dose to be applied transdermally. Preferably, the conclusion of the defined rotation is marked in a way that can be sensed or seen by the user, e.g., through a resistance when turning, or it an optical label.

An grease stick of the invention is preferably solid or highly viscous and can be applied onto the skin with a slight pressure. The grease stick is preferably thixotropic.

The composition according to the invention, e.g. the grease stick, can be contained or fixed in a holding and dosing device (applicator), which can be constructed in a similarmanner as a lipstick sleeve. With the device, the composition can be advanced by a defined length, which corresponds to a transdermally applied dosage unit, e.g., via a defined rotation. Preferably, the completion of this defined rotation is marked in a way it can be felt or seen by the person who is using the device, e.g. by a resistance to turning, or a visual marking.

The composition according to the invention can be a gel or an ointment or a cream. It may be a water-in-oil suspension or an oil-in-water suspension, but in a preferred embodiment, the composition is free of water, more preferably lipophilic and free of water. Gel, ointment or cream are semi-solid and spreadable, preferably also thixotropic. In a preferred embodiment, gel, ointment or cream are contained in an applicator, from which the composition can be pushed from the applicator (e.g., 35-40 µl/dose), e.g. by rotation. It can be a multidose applicator. The applicator may comprise an attachment for administration within the interior of the auricle/pinna, e.g. in brush shape. The composition can also be applied with a glove/fingerling.

A composition formulated according to the invention, e.g. a grease stick or preferably a lipophilic water-free composition, preferably comprises methimazole, beeswax, and a fatty oil such as almond oil, furthermore optionally PVP and/or a nanocarrier. Mixtures of various waxes, particularly of liquid, semi-solid and/or solid PEG can be used to achieve a suitable viscosity. Exemplary basic formulations, to which according to the invention the active substance and optionally an emulsifier are still added, are for example disclosed in WO/2008/009562 or from the manufacture of lipsticks or viscous lipophilic formulations. A dye/pigment does not have to be included.

The inventive composition preferably is a pharmaceutical composition, especially a pharmaceutical composition formulated for transdermal administration.

One object of the invention also is the inventive composition for use in the treatment of hyperthyreosis. A method for the treatment of hyperthyreosis, which comprises transdermally administering an inventive composition to a patient, is also an object of the invention.

According to the invention, hyperthyreosis can be treated in a cat. Alternatively, the patient to be treated is a human, a dog, a horse, a camel, a pig, a cow, a rabbit, a guinea pig, a mouse or a rat.

The composition may be formulated for topical administration in the inside of the auricle, in particular in the inside of the pinna of a cat.

The inventive transdermal composition hat particular advantages in the treatment of hyperthyroidism in older and/or multi-morbid people, because side effects of oral administration of the active compounds can also be avoided here. In people, a transdermal administration e.g. to the inside of the forearm is possible in an uncomplicated way, and allows for self-medication or administration by third parties such as nursing staff.

The inventive composition can be used every second day, daily or twice daily. Long-term therapy (over several months or years) or drug therapy in advance of radiation therapy or, especially in humans, before a thyroidectomy is possible.

A composition for the transdermal administration of an active substance, namely methimazole or carbimazole, to a cat is also subject matter of the invention, wherein the composition is a stick, in particular a grease stick according to the invention. The invention also relates to a composition for the transdermal administration of an active substance, namely methimazole or carbimazole, to a cat, the composition being a cream which is contained in an applicator for administration in the pinna. Preferably, the applicator is a multidose applicator.

The inventors have found that the composition according to the invention renders a significant reduction in the amount of therapeutic agent compared to compositions from the prior art (US 2010/01373838 A1) possible. This is e.g. due to the long-term release of the active ingredient.

The invention is illustrated by the following examples, which are to contribute to the understanding of the invention, but should not limit it. In the context of the invention, "a" always means "one or more", unless this is explicitly excluded. All publications cited herein are incorporated herein in full by reference.

EXAMPLES

Example 1

Preparation of Various Compositions

|  | Z1 |  | Z2 |  | Z3 |  |
|---|---|---|---|---|---|---|
| Active substance | Methimazole | 11.2% | Methimazole | 11.2% | Methimazole | 11.2% |
| Wax | Cera alba | 14.3% | Cera alba | 14.3% | Cera alba | 15.8% |
| Fatty oil | Almond oil | 67.5% | Almond oil | 68.0% | Almond oil | 72.5% |
| Emulsifier | PVP Nanocarrier | 6.5% 0.5% | PVP | 6.5% | Nanocarrier | 0.5% |

|  | Z4 |  | Z5 |  | Z6 |  |
|---|---|---|---|---|---|---|
| Active substance | Methimazole | 11.2% | Methimazole | 11.2% | Methimazole | 11.2% |
| Wax | Cera alba | 16.0% | Cetyl palmitate | 14.0% | Cera alba | 15.8% |
| Fatty oil | Almond oil | 72.8% | Mineral oil | 74.8% | Mineral oil | 72.5% |
| Emulsifier |  | 0% |  | 0% | Nanocarrier | 0.5% |

%: w/w
Nanocarrier: polyglyceroldodecanic acid polyethylenglycolate
PVP: Molecular weight of 10.000 Da to 17.000 Da.

|  | Z7 |  | Z8 |  | Z9 |  |
|---|---|---|---|---|---|---|
| Active substance | Methimazole | 11.2% | Methimazole | 7.6% | Methimazole | 11.2% |
| Wax | Cera alba | 14.3% | Cera alba | 13.4% | Cera alba | 14.3% |
| Fatty oil | Almond oil | 67.5% | Almond oil | 72.0% | Almond oil | 67.5% |
| Emulsifier | PVP Nanocarrier | 6.5% 0.5% | PVP Nanocarrier | 6.5% 0.5% | PVP Nanocarrier | 6.5% 0.0% |

Example 2

A 14-year-old, neutered, hyperthyreotrophic cat was treated with a formulation of type Z7 and Z8 as well as Z9. The TT4 value at the beginning of treatment was 23.7. After 4 weeks of treatment with a dose of 100 μl of formulation type Z7, the TT4 value decreased to a value of 8.7 and the condition of the cat improved significantly. After a dosage increase to 14 mg/day by twicy daily application of type Z8 the value decreased to the lower euthyreotic range. Subsequently, a dose adjustment was made to 11.2 mg per day (type Z9) to achieve a stable value in the middle to upper euthyroid range. The total treatment time was 270 days.

Example 3

Two hyperthyroidic cats were treated with a lipophilic, water-free formulation of type Z7. The dose was 5 mg/day. Both cats had a TT4 value of 8.6±0.5 before treatment and a TT4 value of 3.7-4.3 after 14 days of treatment.

Example 4

Four hyperthyroid cats were administered a lipophilic, water-free formulation of the type Z9. The initial dose was 5.5 mg/day, which was individually adjusted after 28 days to 3.5 mg/day to 5.5 mg. The mean TT4 value of the cats was 9.81 before the treatment.

After 7 to 14 days, the mean TT4 value was 5.7, after 90 days 4.5. The cats were thus in the eurthyroid range, which is between 4.5 and 1.0.

Example 5

Four hyperthyroid cats were administered a formulation of type Z9 for 10 to 14 days. In all cats, a significant reduction in the TT4 value was observed (from originally 9.8±2.2 to 7.4±2.5). The dose was 5.5 mg every 2 days. The TT4 values on treatment-free days did not significantly differ from the TT4 values on days with treatment. This suggests that, surprisingly, the water-free formulation types described in the invention with a sufficient dosage strength can also be used as a sustained-release formulation.

Example 6

The formulations of type Z7 were stored for 90 days at 30° C., 40° C. and 50° C. No reduction of the methimazole content was observed.

Example 7

22.4 g of methimazole and 13.0 g of PVP were rubbed in a fanta dish with a small amount (about 5 g) of oleum amygdalarum (almond oil). 28.60 g of Cera Alba, 1.0 g of nanocarrier and 130 g were melted in a water bath. This was followed by cooling to room temperature with stirring, and the methimazole/PVP mixture was incorporated into the batch.

Example 8

The active substance methimazole was ground with 30 g almond oil and, optionally, the nanocarrier. 30 g of almond oil were melted together with beeswax and almond oil in a water bath and then stirred until cold. The active substance was then incorporated into the ointment base.

The invention claimed is:

1. A composition comprising
   a) 2.5-15% (w/w) of an active agent selected from the group comprising methimazole and/or carbimazole;
   b) 5-18% (w/w) beeswax;
   c) 45-75% (w/w) of at least one fatty oil selected from the group consisting of peanut oil, almond oil, sunflower oil, linseed oil, olive oil, and evening primrose oil; and
   d) 0.25 to 3.5% (w/w) of at least one emulsifier comprising a unimolecular nanocarrier,
   wherein the nanocarrier is composed of a dendritic core and at least two shells;
   wherein an inner shell is coupled to the dendritic core via a first linker, and an outer shell is coupled to the inner shell via a second linker;
   wherein
      a) the dendritic core of the nanocarrier is made of polyglycerol,
      b) the inner shell of the nanocarrier is an alkyl chain with a carbon length of C2 to C40,
      c) the outer shell is polyethylene glycol having the structural formula $(-CH_2-H_2O-)_n$, with n=3-130, which bears a terminal a methyl group, a hydroxyl group or a carboxyl group,
      d) the first linker is an ester or amide linkage,
      e) the second linker is an ester bond,
      or any combination thereof; and
   wherein the composition is free of water.

2. The composition according to claim 1, wherein the active substance is methimazole.

3. The composition according to claim 1, wherein the active substance is carbimazole.

4. The composition according to claim 1, wherein the beeswax is cera alba.

5. The composition according to claim 1, wherein the fatty oil is almond oil.

6. The composition according to claim 1, wherein
   a) the dendritic core of the nanocarrier is made of polyglycerol with a molecular weight of 3-20 kDa;
   b) the inner shell of the nanocarrier is a linear alkyl chain with a carbon length of C2 to C40;
   c) the outer shell is polyethylene glycol having the structural formular $(-CH_2-H_2-)_n$, with n=3-130, which bears a terminal a methyl group, a hydroxyl group or a carboxyl group;
   d) the first linker is an ester or amide linkage;
   e) the second linker is an ester bond;
   or any combination thereof.

7. The composition according to claim 1, wherein the nanocarrier is polyglyceroldodecanic acid polyethylenglycolate or polyglycerol pentadecanoic acid polyethylene glycolate.

8. The composition according to claim 1, further comprising dexpanthenol.

9. The composition according to claim 1, which is a grease stick or comprises a grease stick, or a lipophilic formulation in a suitable applicator or comprising the same.

10. The composition according to claim 1 which is a gel, an ointment, or a cream.

11. The composition according to claim 1, which is a pharmaceutical composition formulated for transdermal administration.

12. A method for the treatment of hyperthyreosis, comprising administering a composition according to claim 1 to a patient.

13. The method of claim 12, comprising transdermally administering the lipophilic composition of claim 9 in an applicator for transdermal delivery of an active substance, selected from the group consisting of methimazole and carbimazole, to a cat.

14. The composition according to claim 1, wherein
   a) the dendritic core of the nanocarrier is made of polyglycerol with a molecular weight of 3-20 kDa;
   b) the inner shell of the nanocarrier is a linear alkyl chain with a carbon length of C8-C14;
   c) the outer shell is polyethylene glycol having the structural formula $(-CH_2-H_2O-)_n$,
   d) the first linker is an ester linkage;
   e) the second linker is an ester bond;
   or any combination thereof.

15. The composition according to claim 1, wherein
   a) the dendritic core of the nanocarrier is made of polyglycerol with a molecular weight of 3-20 kDa;
   b) the inner shell of the nanocarrier is a preferably linear alkyl chain with a carbon length of C2 to C40;
   c) the outer shell is polyethylene glycol having the structural formulat $(-CH_2-H_2-)_n$, with n=3-130, which bears a terminal a methyl group, a hydroxyl group or a carboxyl group;
   d) the first linker is an ester or amide linkage; and
   e) the second linker is an ester bond.

* * * * *